United States Patent [19]

Rüger

[11] Patent Number: 5,013,844

[45] Date of Patent: May 7, 1991

[54] PYRIDINIUM ARYL HYDRAZIDE COMPOUNDS

[75] Inventor: Reinhold Rüger, Rödermark, Fed. Rep. of Germany

[73] Assignee: E. I. Du Pont de Nemours and Company, Wilmington, Del.

[21] Appl. No.: 451,000

[22] Filed: Dec. 15, 1989

Related U.S. Application Data

[62] Division of Ser. No. 393,651, Aug. 14, 1989, Pat. No. 4,937,160.

[30] Foreign Application Priority Data

Aug. 27, 1988 [DE] Fed. Rep. of Germany ....... 3829078
Jun. 28, 1989 [DE] Fed. Rep. of Germany ....... 3921134

[51] Int. Cl.$^5$ ............................................ C07D 213/20
[52] U.S. Cl. ..................................... 546/332; 546/347
[58] Field of Search ................................ 546/347, 332

[56] References Cited

U.S. PATENT DOCUMENTS 2,563,785 8/1951 Ives ........................................ 95/88
3,386,831 6/1968 Honig et al. .......................... 96/109
4,224,401 9/1980 Takada et al. ...................... 96/66 R

FOREIGN PATENT DOCUMENTS 0253665 1/1988 European Pat. Off. ............ 96/66 R
62-275247 11/1987 Japan ................................. 96/66 R

OTHER PUBLICATIONS

Chemical Abstracts, vol. 99, No. 19, Abstract 158195w, p. 596, Nov. 7, 1983 [Katritzky et al.].
Anonymous Research Disclosure, 23510, Nov. 1983.

*Primary Examiner*—Frederick E. Waddell
*Assistant Examiner*—Zinna Northington-Davis

[57] ABSTRACT

Photographic silver halide elements containing aryl hydrazides as defined for the production of images with ultrahigh contrast and a new class of aryl hydrazides with a cationic group in the aryl radical as defined. The photographic silver halide elements can be developed at relatively low pH values and have low fog and low tendency to form black spots in unexposed or slightly exposed areas.

8 Claims, No Drawings

PYRIDINIUM ARYL HYDRAZIDE COMPOUNDS

This is a division of application Ser. No. 07/393,651, filed Aug. 14, 1989, now U.S. Pat. No. 4,937,160.

TECHNICAL FIELD

This invention relates to novel aryl hydrazides.

BACKGROUND OF THE INVENTION

Photographic silver halide systems with ultrahigh contrast are used, for example, in reprography for the production of screened images from halftone recording elements, for photo typesetting technology and for line transparencies and photomasks. The term "ultrahigh" as used herein means that the contrast is higher than can be expected, if it is assumed that each individual emulsion grain is exposed and developed independently of its neighbors. Such systems use, for example, effects in which the development of a grain initiates the development of a neighboring grain even if the latter was not exposed sufficiently to be developable by itself ("infectious development").

So-called litho systems have long been known. These consist of films, in which the greatest proportion of the silver halide is present as chloride, and accompanying developers, which are characterized by a relatively high pH value, a low sulfite content and the absence of superadditive-acting developer compounds. Accordingly, the light sensitivity of the films and their development speed are relatively limited and considerable expense is required to maintain the activity of the developer constant over a longer period of time.

These disadvantages have been mitigated recently in systems introduced commercially, in which systems, the development of the photographic element is conducted in the presence of certain hydrazine compounds. Research Disclosure 23510 (Nov. 1983) presents a summary of the extensive literature on this subject. According to this publication, most so-called activated hydrazine compounds are used. Such compounds can be described by the general formula $CT—NR^1—NR^2—Ac$, wherein CT is a tertiary carbon, mostly as the constituent of an aromatic ring system, such as phenyl; $R^1$ and $R^2$ are alkali cleavable radicals and Ac is an activating group. The hydrazine compounds are usually added to the light sensitive layer of the photographic element. Free hydrazine compounds, which fog adjacent grains, are alleged to be generated by the action of the alkaline developer solution interacting with oxidation products generated from the developer compound in the development of the silver halide grains. In practice, preferred hydrazine compounds are those in which the activating groups are bonded through carbonyl groups to the hydrazo nitrogen. If CT in the above formula is a tertiary carbon in an aromatic group, these compounds are designated as aryl hydrazides.

A disadvantage of the systems using hydrazine compounds is that the development must be conducted at relatively high pH values. Indeed, the relevant publications describe developer pH values in the range from about 9 to 12.5; however, values over 11.5 are used exclusively in practice, because, otherwise, satisfactory development speed is not achieved and image quality is inadequate. In addition, the developer solutions are not stable enough for problem-free processing. In particular, they are very sensitive to atmospheric oxygen, despite their high sulfite content. Likewise, unavoidable slight fluctuations of pH during operation change the development or processing characteristics so strongly that it is difficult to maintain uniform results over a longer period. Further problems are the severe corrosion of the development machines by the highly alkaline developer solutions and the disposal of the comparatively highly buffered, exhausted solutions.

European Patent Application 02 53 665-41 discloses photographic elements that contain hydrazine compounds in which the activating group is split off in the alkaline developer medium with the formation of a ring-shaped structure. These elements can be developed at pH 11 with satisfactory results. The above indicated disadvantages are indeed mitigated hereby; but there exists as before a need for further improvement. Moreover, the particular aryl hydrazides used therein can be prepared only by multistep syntheses or with poor yields.

Although the hydrazine compounds appear today technically superior in many respects in the litho systems, there still exists in particular the need to further accelerate the processing operation, the duration of which is determined decisively by the development time.

Therefore, it is desired to provide photographic silver halide elements with specific hydrazine compounds that can be developed at relatively low pH values comparatively rapidly to ultrahigh contrast. It is also desired to provide elements of this type in which the result of development depends only slightly on pH value. Furthermore, it is desired to provide new hydrazine compounds that are suitable for the preparation of such photographic silver halide elements and can be prepared at low cost with good yield.

SUMMARY OF THE INVENTION

In accordance with this invention there is provided a photographic silver halide element containing an aryl hydrazide for the production of images with ultrahigh contrast comprising a support having thereon at least one silver halide emulsion layer, the emulsion layer or at least one other hydrophilic colloid layer on said support contains an aryl hydrazide of the general formula:

$$Ar—NR—NR^1—G—X^+ \ A^- \qquad (I)$$

wherein

Ar is a substituted phenyl group or another substituted or unsubstituted aryl group, G is CO, SO, $SO_2$, $PO_2$, $PO_3$ and $C{=}NR^2$ X+ is a radical containing a cationic group, R, $R^1$, $R^2$, which can be the same or different, are hydrogen, alkyl of 1 to 6 carbon atoms and alkyl sulfinyl of 1 to 6 carbon atoms, and $A^-$ is an anion.

In accordance with another embodiment of this invention there is provided aryl hydrazides of the formula:

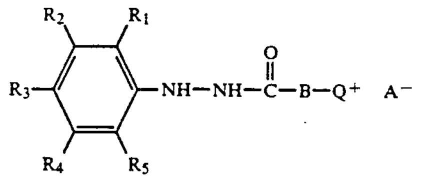

(II)

wherein $R_1$ to $R_5$, which can be the same or different, are hydrogen, alkyl, alkoxy, hydroxyalkyl, haloalkyl, alkylamino, or aliphatic acylamino each with 1 to 20 carbon atoms, or cycloalkyl with 3 to 20 carbon atoms, aryl, aryloxy or aromatic acylamino, each with 6 to 10 carbon atoms, aralkyl, or aralkoxy with 1 to 3 carbon atoms in the alkylene chain or an aliphatic acylamino radical with 1 to 4 carbon atoms substituted by a phenoxy radical which may be substituted by one or more alkyl radicals with 1 to 10 carbon atoms with the proviso that at least one of $R_1$ to $R_5$ is not hydrogen, $Q^+$ is trialkylammonium, pyridinium-1-yl, N-alkylpyridinium-x-yl where x is a whole number of 2, 3 or 4, thiazolinium-3-yl, or N-alkylthiazolinium-x-yl where x is 2, 4 or 5, in which the heterocyclic rings may be substituted by additional alkyl radicals, and in which all alkyl groups of a radical $Q^+$ may be the same or different and/or may be substituted by hydroxyl or sulfonic acid groups, each alkyl group having no more than 12 carbon atoms, but in the case of trialkylammonium, two of them may also form with the quaternary nitrogen a ring with 3 to 12 members, B is a bridge which may be composed of 1 to 3 methylene groups, each of which may be substituted by methyl or ethyl, or if $Q^+$ is N-alkylpyridinium-x-yl or N-alkylthiazolinium-x-yl, may also be an oxygen atom or a single bond, and $A^-$ denotes an anion which is not present when $Q^+$ contains a sulfo group.

DETAILED DESCRIPTION OF THE INVENTION

The radical Ar in the formula $AR—NR—NR^1—G—X^+\ A^-$ can be represented by a substituted phenyl radical and also by a substituted or unsubstituted aryl radical, e.g., a naphthyl, an anthryl or a phenanthryl radical.

The substituents on the aromatic ring system of the radical Ar preferably contain those groups which are used according to the state of the art to impart to the hydrazine compound certain properties such as a certain diffusion capacity (ballast groups) or a certain absorption behavior on the silver halide (absorption promoting groups). Examples of such substituents are unbranched, branched, or cyclic alkyl, alkenyl or alkinyl, preferably with 1 to 20 carbon atoms which, in turn, may also be further substituted by one of the radicals named in this paragraph, e.g., halogen atoms, cyano, carboxyl, amino, substituted or unsubstituted aryl radicals with 6 to 14 carbon atoms, alkylamino and acylamino radicals with 1 to 20 carbon atoms, thiocarbamide radicals and other radicals containing thiocarbonyl groups, alkoxy and aryloxy radicals, aliphatic and aromatic acyloxy radicals, urethane groups, alkyl- and arylsulfonyl, alkyl- and arylsulfonamido radicals as well as radicals of nitrogen or sulfur-containing heterocycles with 5 to 10 members, such as imidazole, thiazole, benzothiazole, benzimidazole, etc. The above-named substituents may be bound to the aryl radical independently of one another or also, while mutually substituting for one another, be connected into a chain which replaces a hydrogen atom of the aryl. Those substituents have a favorable effect which increase the electron density of the aromatic ring system by mesomeric or inductive effects.

The radical $X^+$ contains a group with a permanent positive charge, such as is present, for example, in onium compounds such as ammonium, phosphonium, and oxonium compounds.

The anion $A^-$ may be a halide anion, such as chloride, bromide, or iodide ion or also a complex inorganic ion such as a sulfate or perchlorate or also a common organic anion such as toluene sulfonate or trichloroacetate. Anions of strong acids are preferred. If the hydrazine compound is substituted on a radical with an anionic group, the anion may drop off due to the formation of an internal salt.

On the basis of the current state of the art, the skilled artisan could not have foreseen that the compounds of the invention with cationic groups in the activating radical would have improved properties, particularly a higher development speed at low pH values. Rather, a known comparison experiment with simple hydrazines, Takada et al. U.S. Pat. No. 4,224,401, shows no influence of such a group on the development of contrast. According to Honig et al. U.S. Pat. No. 3,386,831, an aryl hydrazide not substituted on the aryl radical and with a cationic group in the acyl radical has a strong fogging effect on high sensitivity iodobromide emulsions without affecting contrast. In contrast, the elements of the invention show no increase in fog even on long storage and also show ultrahigh contrast with suitable development.

Although a number of different aryl groups comes into consideration for the radical Ar, substituted phenyl groups Ph are preferred because of their easier availability. Accordingly, the preferred aryl hydrazides correspond to the formula:

$$Ph — NR — NR^1 — G — X^+\ A^- \qquad (Ia)$$

where Ph is a substituted phenyl group,

G stands for the groups CO, SO, $SO_2$, $PO_2$, $PO_3$, or $C{=}NR_2$, $X^+$ is a radical containing a cationic group, R, $R^1$, $R^2$, which can be the same or different, are hydrogen, alkyl, or alkylsulfinyl with 1 to 6 carbon atoms, and $A^-$ is an anion.

The substituents on the phenyl group may be the same as named above for the aryl groups Ar.

Also because they are easier to produce, compounds in which the group G is represented by a carbonyl group are preferred. Such compounds are described the formula:

$$Ph — NR — NR^1 — CO — X^+\ A^- \qquad (Ib)$$

where

Ph is a substituted phenyl group, $X^+$ is a radical containing a cationic group, R, $R^1$, which can be the same or different, are hydrogen, alkyl or alkylsulfinyl with 1 to 6 carbon atoms, and $A^-$ is an anion.

Among the radicals $X^+$ which contain a cationic group, those radicals $Y^+$ are preferred in which the positive charge is introduced by a quarternated nitrogen atom, e.g., in an aliphatic or aromatic bond. The corresponding aryl hydrazides are denoted by the formula $$Ph — NR — NR^1 — G — Y^+\ A^- \qquad (Ic)$$

where

Ph is a substituted phenyl group,

G stands for the groups CO, SO, $SO_2$, $PO_2$, $PO_3$, or $C{=}NR^2$, $Y^+$ is a radical containing a cationic group with at least one quarternated nitrogen atom, R, $R^1$, $R^2$ which can be the same or different, are hydrogen, alkyl or alkylsulfinyl with 1 to 6 carbon atoms, and $A^-$ is an anion.

The radical $Y^+$ may represent quarternary ammonium radicals which are bound to G via a straight-chained or possibly branched hydrocarbon chain with 1 to 4 carbon atoms, which may also contain an ether-like bound oxygen atom or also by heterocyclic radicals with quaternary nitrogen. In the latter case the bond of the quaternary nitrogen to G can be achieved both by carbon atoms of the heterocyclic ring system and also by side chain carbon or oxygen atoms. A direct bond of the quarternary nitrogen to G is excluded. Examples of such radicals are trialkylammonium methyl, 2-trialkylammonium ethyl, pyridinium-1-yl-methyl, 1-alkylpyridinium-2-yl, 1-alkylpyridinium-3-yl, 1-alkylpyridinium-4-yl, hydroxyethyldimethylammonium methyl, 4-sulfoethylpyridinium-1-yl-methyl, N-dodecyldimethylammonium methyl-2-methylthiazolinium-3-yl-methyl, N-ethylpyridinium-3-oxymethyl.

During the development work on the invention new aryl hydrazides were found which are described by the general formula (II).

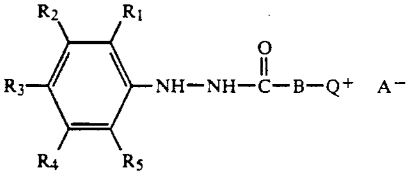

(II)

where $R_1$ to $R_5$ denote radicals which may be the same or different, but of which at least one is not hydrogen, and which are represented by hydrogen, alkyl, alkoxy, hydroxyalkyl, haloalkyl, alkylamino, aliphatic acylamino or cycloalkyl, in each case with 1 to 20 carbon atoms, aryl, aryloxy, or aromatic acylamino in each case with 6 to 10 carbon atoms, aralkyl or aralkoxy with 1 to 3 carbon atoms in the alkylene chain or aliphatic acylamino radicals with 1 to 4 carbon atoms substituted by a phenoxy radical substituted by one or more alkyl radicals with 1 to 10 carbon atoms.

$Q^+$ denotes trialkylammonium or pyridinium-1-yl, or N-alkylpyridinium-x-yl, with x=2, 3, or 4, or thiazolinium-3-yl, or N-alkylthiazolinium-x-yl with x=2, 4, or 5, the heterocyclic rings possibly being substituted by additional alkyl radicals and in which all alkyl groups of a radical $Q^-$ may be the same or different and/or may be substituted by hydroxy or sulfo acid groups, each alkyl group having no more than 12 carbon atoms but in the case of the trialkylammonium, two of them may also form a ring of 3 to 12 members with the quarternary nitrogen, B denotes a bridge which can consist of 1 to 3 methylene groups, each of which may be substituted by methyl or ethyl, or if $Q^+$ is N-alkylpyridinium-x-yl or N-alkylthiazolinium-x-yl, also of an oxygen atom or of a single bond, and $A^-$ is an anion which is not present if $Q^+$ contains a sulfo group. In the following, some examples of the aryl hydrazides of formula (II) according to the invention are listed.

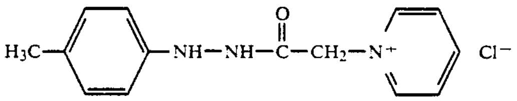

(II-1)

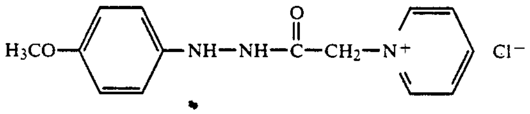

(II-2)

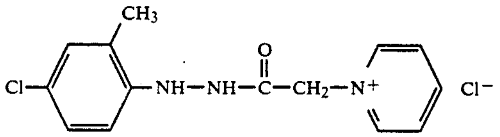

(II-3)

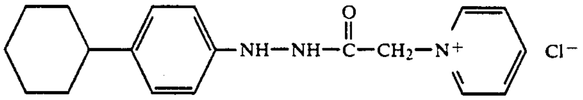

(II-4)

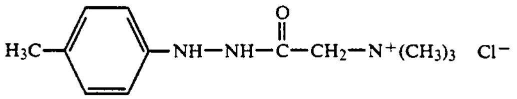

(II-5)

-continued
(II-6)
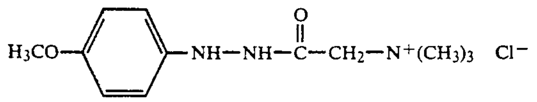
(II-7)
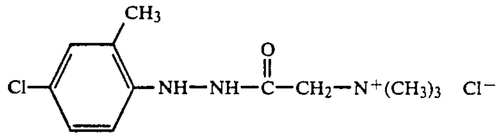
(II-8)
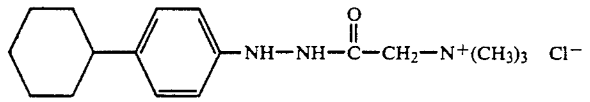
(II-9)
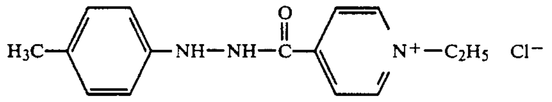
(II-10)
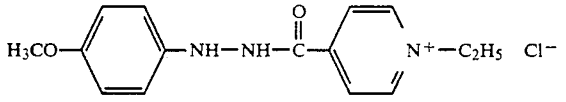
(II-11)
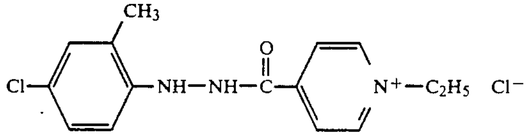
(II-12)
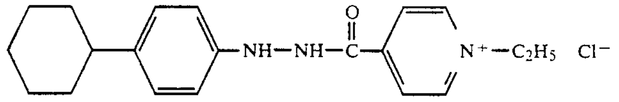
(II-13)
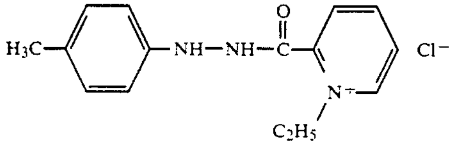
(II-14)
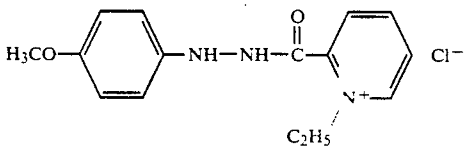
(II-15)
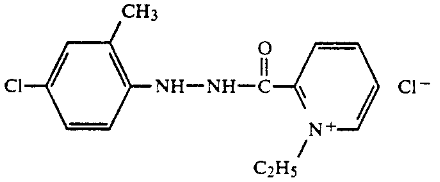
(II-16)
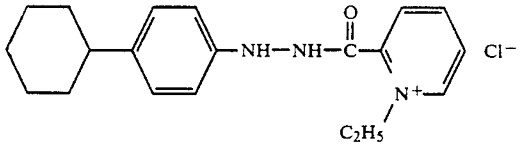

-continued
(II-17)
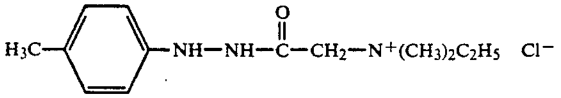
(II-18)
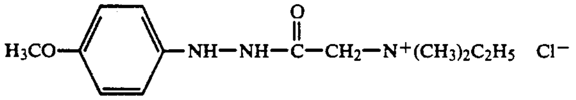
(II-19)
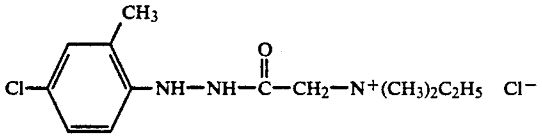
(II-20)
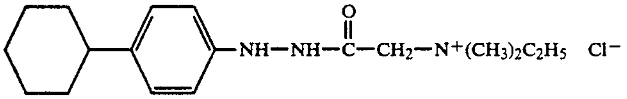
(II-21)
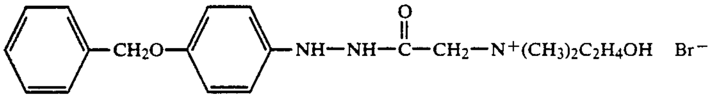
(II-22)
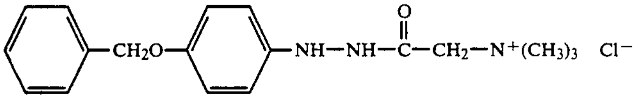
(II-23)
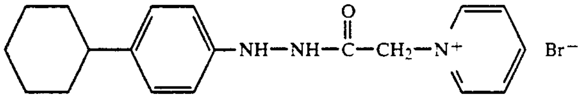
(II-24)
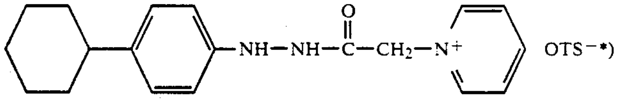
(II-25)
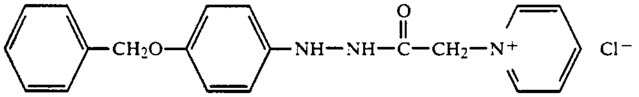
(II-26)
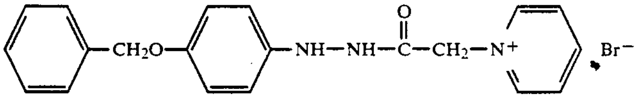
(II-27)
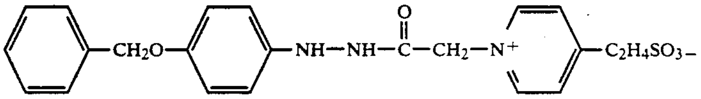
(II-28)
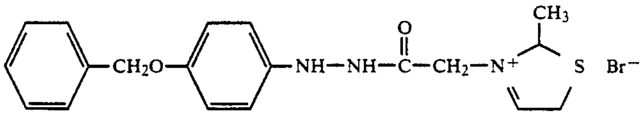
(II-29)
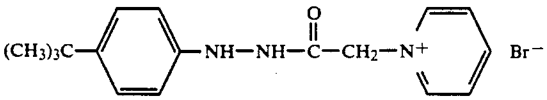

-continued

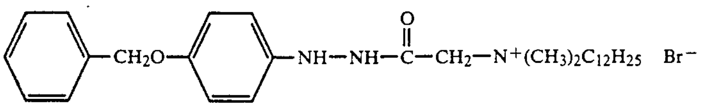

(II-30)

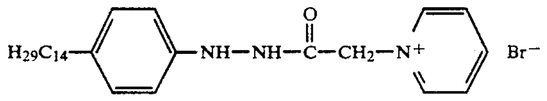

(II-31)

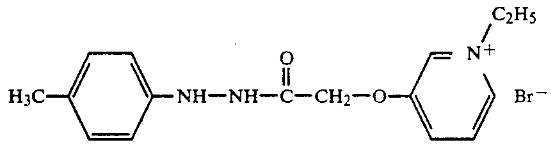

(II-32)

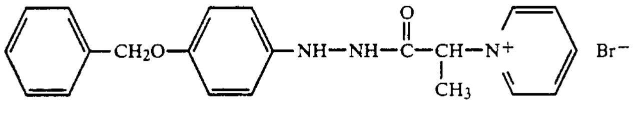

(II-33)

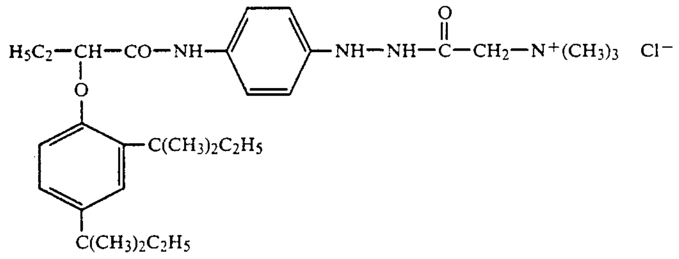

(II-34)

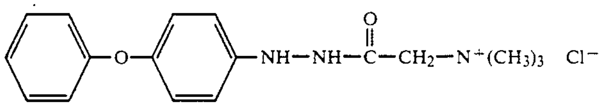

(II-35)

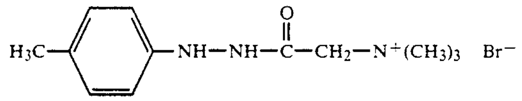

(II-36)

*p-Toluolsulfonat-Anion

The aryl hydrazides according to the invention can be synthesized by various processes in a simple way, e.g., from equimolar quantities of the aryl hydrazine, with the corresponding carboxylic acid and dicyclohexylcarbodiimide (cf. Methoden der Organischen Chemie (Houben-Weyl), 4th edition, Vol. X/2, page 355). Another way of incorporating the aryl radical into the hydrazide leads via quinone monoacyl hydrazones and quinone oxime monoacyl hydrazones (cf. Houben-Weyl, same volume, page 233). A third possibility consists in the hydrazinolysis of carboxylic acid esters (Houben-Weyl, same volume, page 360 f.). Other possibilities of synthesis are known to the expert.

An especially preferred version of the invention is represented by photographic silver halide elements which contain compounds of general formula (II).

The light sensitive silver halides that can be present in the elements of the invention include: silver chloride, silver bromide, silver chlorobromide, silver bromoiodide or silver chlorobromoiodide, etc. These can be monodisperse or polydisperse and can have a homogeneous composition, but can also have grains with core-shell structures as well as be mixtures of grains of different composition and grain size distribution. They are prepared with the use of a hydrophilic colloidal binder, preferably gelatin. Methods for the preparation of suitable light sensitive silver halide emulsions are known to those of ordinary skill in the art, and are summarized, for example, in Research Disclosure 178,043, Sections I and II, the disclosures of which are incorporated herein by reference.

Silver halide emulsions, which are prepared by controlled double jet precipitation, have a cubic grain shape and with a chloride proportion less than 50 mole percent, are preferred for the element of the invention.

The grain size of the emulsions is selected according to the required sensitivity and can be between 0.1 and 0.7 μm edge length, the preferred range being between 0.15 and 0.30 μm edge length. In the preparation of the emulsion, noble metals salts, particularly rhodium or iridium salts, can be present in the usual quantities to improve photographic properties.

The preferred emulsions are chemically sensitized. Suitable methods of sensitization are sulfur, reduction and noble metal sensitization, which can also be used in combinations. In the latter, iridium compounds for example, can be used. The emulsions can be spectrally sensitized with conventional sensitizing dyes.

The emulsions can also contain the usual antifoggants. Substituted benzotriazole, 5-nitroindazole and mercury chloride are preferred, as desired. These agents can be added at any time during the emulsion preparation or can be contained in an auxiliary layer of the photographic element. For improvement of the photographic properties, an iodide in a quantity of about 1 mmol per mole of silver can be added to the emulsion before or after chemical ripening.

The emulsions can also contain known polymer dispersions that improve, for example, the dimensional stability of the photographic element. These usually involve lattices of hydrophobic polymers in an aqueous matrix. Examples of suitable polymer dispersions are disclosed in Research Disclosure 176,043 Section IXB (Dec. 1978) the disclosure of which is incorporated herein by reference.

The light sensitive layers of the photographic elements can be hardened with known agents. The hardening agent can be added to the emulsion or incorporated in an auxiliary layer, for example, an outer protective layer. A preferred hardening agent is hydroxydichlorotriazine.

The photographic element can contain further additives that are known and customary for the production of specific properties. For example, such agents are shown in Research Disclosure 176,043 in Section V (brighteners), XI (coating aids), XII (plasticizers and slip agents) and XVI (matte agents), the disclosures of which are incorporated herein by reference.

The gelatin content of the emulsions lies generally between 50 and 200 g per mole of silver; the range between 70 and 150 g per mole of silver is preferred.

The aryl hydrazides of the invention are preferably incorporated in the emulsion, but can also be contained in an auxiliary layer in contact with the emulsion layer. For example, a solution of the aryl hydrazide is added to one of the coating solutions. Addition to the emulsion takes place optionally preferably after chemical ripening, but can also take place at any other time. A suitable solvent for the aryl hydrazides of the invention is, for example, ethanol. The concentration of the compounds in the film can be varied over a wide range and is a function of the effectiveness of the compound and the dependency, known to one of ordinary skill in the art, of the infectious development on the remaining composition of the film, for example, the binder content and binder composition, the halide composition and the grain size of the emulsion, the degree of chemical ripening of the emulsion and the type and quantity of stabilization. An accurate coordination of the quantity with the cited parameters is easily determined by one having ordinary skill in the art. The concentration of the compounds can lie in the range between $10^{-5}$ mole/mole of silver to $5\times10^{-2}$ mole/mole of silver and is preferred in the range between $5\times10^{-4}$ and $10^{-2}$ mole/mole of silver.

The above-described layers can be coated by known methods onto photographic film or other supports known to those skilled in the art. Polyethylene terephthalate is a preferred support but the invention is not limited to this support.

Developer solutions that contain the preferred dihydroxybenzenes, such as hydroquinone, as the developer compound are used to process the elements of the invention. In addition, the developer solutions can contain other, also superadditive-acting developer compounds, such as 1-phenylpyrazolidinone or N-methyl-p-aminophenol, and known antifoggants. The sulfite content is preferably over 0.15 mole/liter. Development is conducted preferably in the presence of other contrast-augmenting agents, such as, for example, alkanolamines or secondary aliphatic or aromatic alcohols. The developer temperature lies between 15 and 50° C., preferably between 30° and 45° C. The developer solution has a pH value between 9 and 12.5, the range between 10 and 11.5 being preferred. Depending on development temperature, development time can be 10 to 500 seconds.

Fixing, washing and drying can be conducted by known and practiced methods.

INDUSTRIAL APPLICABILITY

The photographic silver halide elements of the invention can be developed at relatively low pH values and short development times to ultrahigh contrast and outstanding dot quality. They have low fog and low tendency to form black spots, known to the expert as "pepper", in the unexposed or only slightly exposed areas. The influence of the developer pH value on development speed and sensitivity is particularly low in the region of pH 11, so that slight pH variations, unavoidable in practice, do not noticeably affect the photographic result.

With respect to current state-of-the-art hydrazine compounds, particularly the formyl hydrazides with similar chemical structure, the aryl hydrazides of the invention show greater effectiveness as nucleation agents. Therefore, they can be used in lower quantities. Their preparation is possible easily from readily available starting compounds.

Because the elements of the invention require development pH values lower than for elements of the current state of the art, there are advantages from the standpoint of rate of replenishment, disposal of exhausted solutions and corrosion resistance of the development or processing machines.

The preferred field of use of the elements of the invention is reprography, particularly the preparation of screen images from halftone images by conventional or electronic methods, the reproduction of line images and photomasks for printed circuits or other products for photofabrication, as well as the production of printed manuscripts by phototypesetting technology. The aryl hydrazides of the invention can be used preferably with light sensitive silver halides.

Although the invention is oriented to photographic silver halide elements containing aryl hydrazides, it does not exclude a method by which the aryl hydrazides are also contained in the developer solution.

EXAMPLES

The following examples illustrate but do not limit the invention.

Example 1

Preparation of 2-p-tolyl-1-acetohydrazopyridinium chloride (Compound II-1)

8.7 g (0.05 mole) carboxymethylpyridinium chloride and 6.1 g (0.05 mole) p-tolylhydrazine were dissolved in 30 ml methanol. 10.3 g (0.05 mole) cyclohexylcarbodiimide were dissolved in 30 ml tetrahydrofurane and were added slowly to the methanol solution with stirring at room temperature. The mixture was stirred for 2 more hours and then cooled to −18° C. After 24 hours, the yellow solid was separated and extracted with 50 ml of a methanol-water mixture (9 to 1). The product dissolved in this, leaving a residue of dicyclohexylcarbamide. The extract was cooled to −18° C. and filtered after 16 hours. The mother liquor of the reaction mixture was concentrated to a half, let stand 2 days at −18° C., the solid phase was filtered off and combined with the first fraction. Yield: 8 g (58% of theoretical).

Example 2

Preparation of 2-p-methoxyphenyl-1-acetohydrazopyridinium chloride (Compound II-2)

The method described in Example 1 was repeated starting with 8.7 g (0.05 mole) carboxymethylpyridinium chloride, 6.9 g (0.05 mole) p-methoxyphenylhydrazine and 10.3 g (0.05 mole) dicyclohexylcarbodiimide. Yield: 8.9 g of a reddish solid (61% of theoretical).

Example 3

Preparation of 2-p-tolyl-1-acetohydrazotrimethylammonium chloride (Compound II-5)

Example 1 as described was repeated starting with 7.9 g (0.05 mole) p-tolylhydrazine hydrochloride, 5.9 g (0.05 mole) betaine (anhydrous) and 10.3 g (0.05 mole) cyclohexylcarbodiimide. Yield: 6.5 g of a yellow solid (48% of theoretical).

Example 4

Preparation of 2-tolyl-1-(2'-pyridyl)-acetohydrazide (Comparison compound D)

6.1 g (0.05 mole) tolylhydrazine, 6.9 g (0.05 mole) 2-pyridylacetic acid, and 10.3 g (0.05 mole) dicyclohexylcarbodiimide were processed as described in Example 1, except that the reaction mixture was stirred only 1 hour at 60° C. and diluted with 20 ml water before cooling. Yield: 9.7 g (80% of theoretical).

The following reference substances from the state of the art were used in the Examples below:

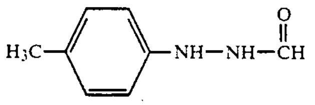
(A)

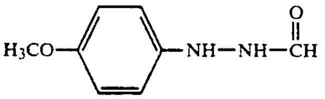
(B)

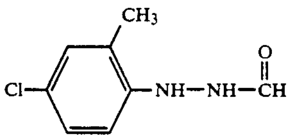
(C)

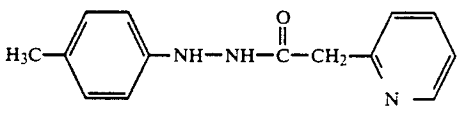
(D)

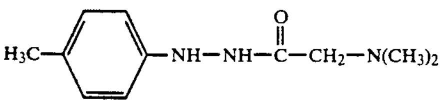
(E)

-continued

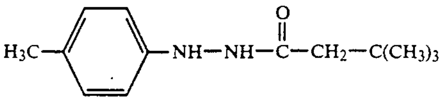
(F)

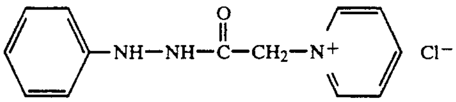
(G)

Example 5

A silver iodobromide emulsion (2 mole percent iodide) with cubic grains of 0.25 μm average edge length was prepared by pAg-controlled double jet precipitation. The emulsion was washed and sensitized chemically in the presence of 0.11 mmole of sodium thiosulfate per mole of silver halide. Then there were added to it the usual quantities of benzotriazole and 5-nitroindazole as antifoggants, a sensitizing dye for the green region of the spectrum in an amount to provide maximum speed, a polyethyl acrylate dispersion, 10% based on the weight of gelatin, and the usual coating aids. The emulsion contained 80 g gelatin per mole silver halide. Equal portions of this basic emulsion were added to ethanol solutions of the compounds set out above and coated on a polyethylene terephthalate film base provided with an antihalation layer. Simultaneously, a gelatin protective layer (1 g/m$^2$ dry weight), also containing a hardening agent, was applied. The experimental films thus prepared contained 4.4 g silver/m$^2$.

The film samples were exposed with white light and in contact with a transparency that consisted of a halftone wedge and a halftone wedge with a contact screen underlay. Processing took place in a developing machine (Duerr Graphica) with Kodak Ultratec developer (pH 11.6) at 38° C. for a development time of 30 seconds.

The following criteria for evaluation were measured on the processed film samples:

density from fog and base ($D_{min}$)
maximum density ($D_{max}$)
relative sensitivity [S, as −10×1 g (I×t) at density 3.0]
contrast between the densities 1.0 and 3.0 (gamma)
dot quality (PQ, from 1 — worst to 10 — best).

The results of the evaluation set out in Table 1 below show that the compounds of the invention work as well in relatively low quantities as known compounds, if developed at pH 11.6.

TABLE 1

| Sample | Compound | | | | | | |
|---|---|---|---|---|---|---|---|
| No. | No. | Amt.[1] | $D_{min}$ | $D_{max}$ | S | Gamma | PQ |
| 1 | II-1 | 1.25 | 0.04 | 4.6 | 9.1 | >25 | 8 |
| 2 | II-1 | 2.5 | 0.04 | 4.7 | 10.2 | >25 | 8 |
| 3 | II-5 | 2.5 | 0.04 | 4.5 | 8.0 | 18 | 8 |
| 4 | II-5 | 5.0 | 0.05 | 4.6 | 8.5 | 22 | 8 |
| 5 | II-2 | 0.6 | 0.06 | 4.6 | 10.5 | >25 | 9 |
| 6 | II-2 | 1.2 | 0.06 | 4.5 | 11.2 | >25 | 9 |
| 7 | II-3 | 2.0 | 0.06 | 4.6 | 9.0 | 25 | 9 |
| 8 | II-3 | 4.0 | 0.06 | 4.6 | 9.6 | 25 | 9 |
| 9 | II-7 | 2.5 | 0.04 | 4.4 | 7.6 | 14 | 7 |
| 10 | II-7 | 5.0 | 0.05 | 4.4 | 8.0 | 16 | 8 |
| 11 | II-4 | 1.25 | 0.05 | 4.6 | 9.6 | >25 | 10 |
| 12 | II-4 | 2.5 | 0.05 | 4.5 | 10.6 | >25 | 10 |
| 13 | II-8 | 1.25 | 0.05 | 4.7 | 8.4 | 18 | 10 |
| 14 | II-8 | 2.5 | 0.05 | 4.5 | 9.3 | >25 | 10 |
| 15 | A | 4 | 0.05 | 4.5 | 9.1 | >25 | 8 |

TABLE 1-continued

| Sample No. | Compound No. | Compound Amt.[1] | $D_{min}$ | $D_{max}$ | S | Gamma | PQ |
|---|---|---|---|---|---|---|---|
| 16 | A | 8 | 0.05 | 4.7 | 9.8 | >25 | 8 |
| 17 | B | 2.5 | 0.05 | 4.5 | 10.2 | >25 | 9 |
| 18 | B | 5.0 | 0.06 | 4.6 | 11.6 | >25 | 9 |
| 19 | C | 5.0 | 0.05 | 4.3 | 7.8 | 16 | 8 |
| 20 | C | 10 | 0.05 | 4.5 | 8.6 | 22 | 9 |

[1]mmoles compound/mole silver halide

Example 6

The testing and evaluation described in Example 5 was repeated with some film samples. However, the pH value of the developer was changed by addition of sulfuric acid or potassium hydroxide. Development time was 40 seconds at 38° C. Results are shown in Table 2 below.

TABLE 2

| Sample | Compound | | pH 10.8 | | pH 11.6 | | pH 12.3 | |
|---|---|---|---|---|---|---|---|---|
| No. | No. | Amt.* | S | Gamma | S | Gamma | S | Gamma |
| 1 | II-1 | 2.5 | 9.4 | 23.0 | 10.8 | >25.0 | | ** |
| 16 (Control) | A | 8.0 | 3.0 | 4.6 | 10.6 | >25.0 | | ** |
| 22 (Control) | D | 10.0 | 2.8 | 3.6 | 3.4 | 3.6 | 9.0 | 18.0 |

*amount in mmoles compound/mole silver halide
**not measured because of high fog The results set out in Table 2 show that the compound II-1 of the invention produces even at pH 10.8 an ultrahigh contrast at higher sensitivity. Consequently, the result is only slightly affected by the change of the pH value from 10.8 to 11.6.

Example 7

Film samples from Example 5 were exposed as described therein and processed in a developer of the following composition for 40 seconds at 39° C.:

| Ingredient | Amount (g) |
|---|---|
| Water | 700.0 ml |
| Potassium hydroxide | 60.0 |
| Sodium disulfite | 76.0 |
| Potassium bromide | 3.3 |
| 5-Methylbenzotriazole | 1.0 |
| Hydroquinone | 30.0 |
| Sodium carbonate monohydrate | 74.0 |
| 3-piperidino-1,2-propanediol | 24.0 |

The pH value was adjusted to 10.8 and water added to make 1 liter. The results are shown in Table 3 below.

TABLE 3

| Sample No. | Compound No. | Compound Amt. | $D_{min}$ | $D_{max}$ | S | Gamma | PQ |
|---|---|---|---|---|---|---|---|
| 1 | II-1 | 1.25 | 0.04 | 4.3 | 6.6 | 13 | 7 |
| 2 | II-1 | 2.5 | 0.04 | 4.4 | 7.6 | 20 | 8 |
| 5 | II-2 | 0.6 | 0.04 | 4.4 | 8.0 | 18 | 8 |
| 6 | II-2 | 1.2 | 0.04 | 4.8 | 9.0 | 22 | 9 |
| 11 | II-4 | 1.25 | 0.04 | 4.2 | 7.1 | 14 | 8 |
| 12 | II-4 | 2.5 | 0.04 | 4.8 | 7.3 | 15 | 9 |
| 16 (Control) | A | 8.0 | 0.04 | 4.2 | 3.3 | 6 | 3 |

The results of this experiment listed in Table 3 show that films, which contain one of the compounds of the invention, indeed yield ultrahigh contrast and good dot quality at a pH value customary for litho and line developers. This result is not achieved with control compound A of the current state of the art.

Example 8

Synthesis of 1-(4-benzyloxyphenyl)-2-(acetodimethyl-(2-hydroxyethyl)-ammonium)hydrazide bromide (compound II-21)

Carboethoxymethyldimethyl-(2-hydroxyethyl)ammonium bromide is obtained by reacting equimolar quantities of bromoacetic acid ethylester with dimethyl-(2-hydroxyethyl)amine in acetone at room temperature as a white crystalline solid and used without further purification after isolation and drying.

0.05 mole (11.4 g) of benzyloxyphenylhydrazine hydrochloride are suspended in 50 ml of dry methanol and mixed with 9.1 ml of a 5.5 m sodium methanolate solution in methanol. The mixture is boiled on reflux for 15 minutes, chilled, and mixed with 15.4 g of carboethoxymethyldimethyl-(2-hydroxyethyl) ammonium bromide (20% excess). The mixture is boiled for 8 hours on reflux, then filtered hot and chilled to induce crystallization. A yellow solid precipitates out which is washed with water and re-crystallized out of methanol. The yield is 11 g (ca. 51% of theoretical).

Example 9

Synthesis of 1-(4-benzyloxphenyl)-2-(acetopyridinium) hydrazide-bromide (compound II-26)

Carbomethoxymethylpyridinium bromide is synthesized by reacting bromoacetic acid methylester with dry pyridine in acetone at room temperature. The product precipitates out as a white crystalline solid during the reaction and can be used without further purification.

34 g (0.15 mole) of benzyloxyphenylhydrazine hydrochloride are suspended in dry methanol in a 2-necked flask with a magnetic stirrer and cooler. To this 27.2 ml of 5.5 m sodium methanolate solution in methanol are added in drops. The reaction mixture is then boiled on the reflux for 30 minutes, brought back to room temperature and mixed with 41 g (0.177 mole) of carbomethoxymethylpyridinium bromide (solid). The mixture turns yellow immediately. It is boiled another 8 hours on reflux, then filtered free of the precipitated table salt and the filtrate allowed to stand in the cold overnight to induce crystallization.

The precipitated-out yellow solid is pipetted off and washed, first with tetrahydrofuran and then with water. The filtrate of the reaction mixture is concentrated and left in the cold once more, at which time more product precipitates out which is isolated and combined with the first fraction. It is recrystallized out of methanol for purification.

Yield: yellow needles, m.p. 207° C., yield: 40 g ca. 64% of theoretical.

Example 10

Synthesis of 2-p-cyclohexyl-1-acetohydrazidopyridinium chloride (compound II-4)

Starting with p-cyclohexylphenylhydrazine and carboxymethylpyridinium chloride, II-4 was synthesized by the process reported for II-1. Batch size: 0.05 mole, yield: 7.5 g, ca. 45% of theoretical, yellowish needles out of methanol, m.p. 237° C.

Example 11

Synthesis of 2-p-cyclohexyl-1-acetylhydrazidopyridinium-p-toluene sulfonate (compound II-24)

1 g of compound II-4 was dissolved in 100 ml of hot water. 0.7 g of sodium toluene sulfonate (20% excess) was added to the hot solution. A voluminous white precipitate formed immediately. The mixture was slowly cooled to room temperature with stirring. The white precipitate was removed by filtration, washed with water and recrystallized out of methanol.

Yield: 1.1 g, ca. 78% of theoretical, m.p. 204° to 206° C.

Example 12

Synthesis of 2-p-benzyloxyphenyl-1-acetohydrazidepyridinium-4-ethyl-β-sulfonate) (compound II-27)

0.05 mole (9.4 g) of β-(4-pyridyl)-ethanesulfonic acid in 50 ml of methanol were neutralized with the equimolar quantity of sodium methanolate and then mixed with 0.05 mole (7.65 g) of bromoacetic acid methyl ester. The mixture was stirred on reflux for 1 hour and then chilled to room temperature. The mixture was filtered free of precipitated sodium bromide. The filter obtained was placed in a suspension of 0.05 mole (10.7 g) of 4-benzyl-oxyphenylhydrazine in 50 ml of methanol and boiled for 12 hours on reflux. After cooling the reaction mixture was concentrated to half its volume and chilled to 18° C. A yellowish-brown precipitate formed which was washed with acetone and ether and recrystallized out of methanol.

Yield: 8 g (ca. 36% of theoretical).

Example 13

A silver bromide emulsion with cubic grain of 0.25 μm average edge length was synthesized by pAg-controlled double jet precipitation. The emulsion was washed and sensitized chemically in the presence of 0.16 mmole of sodium thiosulfate per mole of silver halide. Then the usual quantities of benzotriazole and 5-nitroindazole were added to it as antifogging agents, followed by a sensitizing pigment for the green spectral range, $2.3\times10^{-}$ moles of potassium iodide per mole of silver, polyethyl acrylate dispersion, 10% based on the weight of gelatin, as well as the usual coating aids. The emulsion contained 80 g of gelatin per mole of silver. Equal parts of the base emulsion were mixed with solutions of the compounds named in Table 4 below in ethanol. Then as described in Example 5, test films were produced from the emulsions. Samples from these films were then exposed as described in Example 5. The films were then developed in a Duerr Graphica developing machine with Kodak Ultratec developer whose pH had been adjusted in advance by the addition of sulfuric acid to 10.8 at a temperature of 38° C. for 30 seconds. The evaluation was performed in the same manner as described in Example 5.

The results are summarized in Table 4 below.

From the results, one sees that the compounds according to the invention produce ultrahigh gradations and good dot quality at pH values below 11. A comparison of samples No. 10, 12, and 14, as well as 16 with 18 shows that the counterion had no significant effect on the performance of the compounds according to the invention. Samples 19 and 20 prove that the charge compensation can also be accomplished with an intramolecular anionic group.

Ultrahigh gradation and good dot qualities are not achieved with the reference compounds. The comparison of compounds II-1 with reference compounds A and G shows that only in the case of the simultaneous presence of a cationic group $Q^-$ and a substituted phenyl group Ph does the advantageous effect occur. A comparison of compounds II-36 with reference amino compound E which carries no permanent positive charge, and with reference compound F which contains a carboxylic acid radical which is isoelectronic to the radical contained in compound II-36 but uncharged also shows the advantageous effect of the positive charge.

TABLE 4

| Sample No. | Compound Number | Quantity | $D_{min}$ | $D_{max}$ | S | Gamma | PQ |
|---|---|---|---|---|---|---|---|
| 1 | II-1 | 0.65 | 0.05 | 4.6 | 11.3 | 22 | 7 |
| 2 | II-1 | 1.3 | 0.05 | 5.2 | 12.4 | >25 | 8 |
| 3 | II-17 | 0.65 | 0.05 | 4.8 | 10.0 | 20 | 7 |
| 4 | II-17 | 1.3 | 0.05 | 5.0 | 11.2 | >25 | 8 |
| 5 | II-21 | 0.65 | 0.05 | 4.4 | 8.5 | 14 | 9 |
| 6 | II-21 | 1.3 | 0.05 | 4.9 | 9.7 | 17 | 9 |
| 7 | II-22 | 0.65 | 0.04 | 5.0 | 9.0 | 17 | 9-10 |
| 8 | II-22 | 1.3 | 0.04 | 5.2 | 10.2 | 19 | 10 |
| 9 | II-4 | 0.65 | 0.05 | 5.0 | 10.0 | 17 | 9-10 |
| 10 | II-4 | 1.3 | 0.04 | 5.3 | 11.0 | >25 | 10 |
| 11 | II-23 | 0.65 | 0.04 | 4.9 | 9.6 | 20 | 9-10 |
| 12 | II-23 | 1.3 | 0.04 | 5.2 | 10.5 | >25 | 10 |
| 13 | II-24 | 0.65 | 0.05 | 4.9 | 10.0 | 18 | 9-10 |
| 14 | II-24 | 1.3 | 0.04 | 5.3 | 10.9 | >25 | 10 |
| 15 | II-25 | 0.5 | 0.05 | 4.8 | 11.0 | 19 | 10 |
| 16 | II-25 | 1.0 | 0.04 | 5.3 | 12.0 | >25 | 10 |
| 17 | II-26 | 0.5 | 0.05 | 4.8 | 11.3 | 22 | 10 |
| 18 | II-26 | 1.0 | 0.05 | 5.2 | 12.4 | >25 | 10 |
| 19 | II-27 | 0.65 | 0.04 | 4.7 | 8.2 | 15 | 9-10 |
| 20 | II-27 | 1.3 | 0.04 | 5.1 | 9.3 | 22 | 10 |
| 21 | II-28 | 1.30 | 0.05 | 5.3 | 10.4 | 18 | 10 |
| 22 | II-29 | 0.65 | 0.04 | 4.7 | 10.0 | 20 | 9 |
| 23 | II-29 | 1.3 | 0.04 | 5.3 | 10.8 | >25 | 9-10 |
| 24 | II-30 | 1.5 | 0.04 | 4.4 | 6.5 | 7 | 6 |
| 25 | II-30 | 3.0 | 0.04 | 4.7 | 9.6 | 16 | 9 |
| 26 | II-31 | 3.0 | 0.05 | 4.8 | 8.0 | 12 | 8 |
| 27 | II-32 | 1.3 | 0.05 | 5.3 | 11.1 | >25 | 8 |
| 28 | II-33 | 1.0 | 0.04 | 5.0 | 10.3 | 16 | 9-10 |
| 29 | II-34 | 2.0 | 0.05 | 4.7 | 9.0 | 14 | 9 |
| 30 | II-35 | 0.65 | 0.05 | 5.2 | 8.5 | 9 | 8-9 |
| 31 | II-35 | 1.30 | 0.05 | 5.3 | 10.3 | 16 | 10 |
| 32 | II-36 | 0.65 | 0.05 | 4.9 | 9.5 | 14 | 7 |
| 33 | II-36 | 1.30 | 0.05 | 5.2 | 10.9 | 22 | 8 |
| 34 | None | Trace | 0.04 | 4.20 | 4.0 | 4.5 | 4 |
| 35 | A | 2 | 0.04 | 4.10 | 5.7 | 5.3 | 4 |
| 36 | A | 4 | 0.05 | 4.80 | 6.8 | 6.1 | 4 |
| 37 | A | 8 | 0.05 | 4.60 | 8.1 | 7.4 | 4 |
| 38 | E | 4 | 0.04 | 4.4 | 4.5 | 5.4 | 4 |
| 39 | E | 8 | 0.05 | 4.4 | 4.7 | 6.0 | 4 |
| 40 | F | 4 | 0.04 | 4.10 | 3.90 | 4.7 | 4 |
| 41 | F | 8 | 0.04 | 4.20 | 3.80 | 4.7 | 4 |
| 42 | G | 0.65 | 0.05 | 4.9 | 7.0 | 5.8 | 4 |
| 43 | G | 1.30 | 0.05 | 5.0 | 8.0 | 6.5 | 4 |
| 44 | G | 4.0 | 0.06 | 5.0 | 9.3 | 8.2 | 4 |

I claim:

1. Aryl hydrazides of the formula:

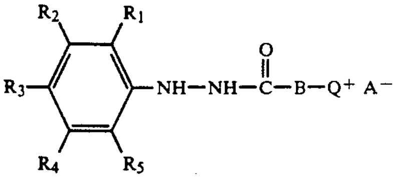

(II)

wherein

R1 to R5, which can be the same or different, are hydrogen, alkyl, alkoxy, hydroxyalkyl, haloalkyl, alkylamino, or aliphatic acylamino each with 1 to 20 carbon atoms, or cyloalkyl with 3 to 20 carbon atoms, aryl, aryloxy or aromatic acylamino, each with 6 to 10 carbon atoms, aralky, or aralkoxy with 1 to 3 carbon atoms in the alkylene chain or an aliphatic acylamino radical with 1 to 4 carbon atoms substituted by a phenoxy radical which may be substituted by one or more alkyl radicals with 1 to 10 carbon atoms with the proviso that at least one of $R_1$ to $R_5$ is not hydrogen.

$Q^+$ is pyridinium-1-yl, N-alkylpyridinium-x-yl where x is a whole number of 2, 3 or 4 in which the heterocyclic rings may be substituted by additional alkyl radicals, and in which all alkyl groups of a radical $Q^+$ may be the same or different and may be substituted by hydroxyl or sulfyl acid groups, each alkyl group having no more than 12 carbon atoms, but in the case of trialkylammonium, two of them may also form with the quaternary nitrogen a ring with 3 to 12 members, B is a bridge which may be composed of 1 to 3 methylene groups, each of which may be substituted by methyl or ethyl, or if $Q^+$ is N-alkylpyridinium-x-yl may also be an oxygen atom or a single bond, and $A^-$ denotes an anion which is not present when $Q^+$ contains a sulfo group.

2. Aryl hydrazide according to claim 1 wherein $Q^+$ is pyridinium-1-yl.

3. Aryl hydrazide compound according to claim 2 of the formula

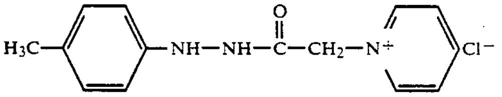

(II-1)

4. Aryl hydrazide compound according to claim 2 of the formula

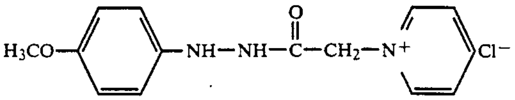

(II-2)

5. Aryl hydrazide compound according to claim 2 of the formula

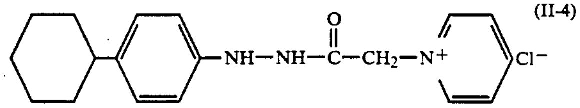

(II-4)

6. Aryl hydrazide compound according to claim 2 of the formula

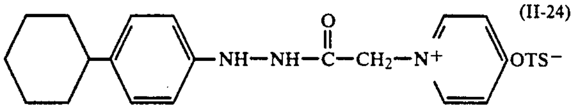

(II-24)

7. Aryl hydrazide compound according to claim 2 of the formula

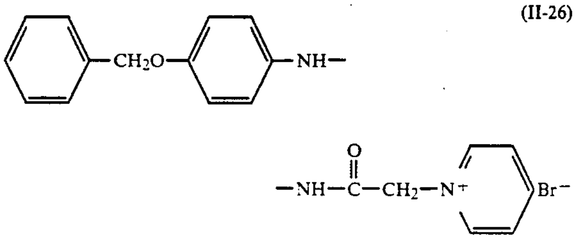

(II-26)

8. Aryl hydrazide compound according to claim 2 of the formula

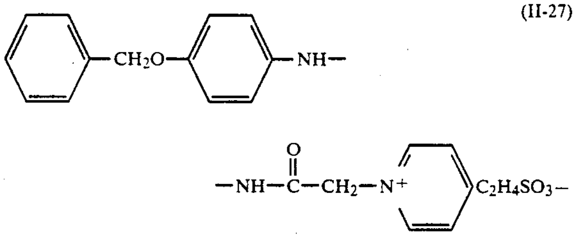

(II-27)

* * * * *